(12) United States Patent
Hironaka et al.

(10) Patent No.: US 11,428,669 B2
(45) Date of Patent: Aug. 30, 2022

(54) RESONANT SENSOR

(71) Applicant: FUJIFILM Corporation, Tokyo (JP)

(72) Inventors: Koji Hironaka, Kanagawa (JP); Fumihiko Mochizuki, Kanagawa (JP); Koji Takaku, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 327 days.

(21) Appl. No.: 16/745,374

(22) Filed: Jan. 17, 2020

(65) Prior Publication Data

US 2020/0150089 A1 May 14, 2020

Related U.S. Application Data

(63) Continuation of application No. PCT/JP2018/027636, filed on Jul. 24, 2018.

(30) Foreign Application Priority Data

Jul. 28, 2017 (JP) .............................. JP2017-146667

(51) Int. Cl.
*G01N 29/02* (2006.01)
*A61B 5/1477* (2006.01)
(Continued)

(52) U.S. Cl.
CPC .......... *G01N 29/022* (2013.01); *A61B 5/1477* (2013.01); *A61B 5/443* (2013.01); *C09D 149/00* (2013.01); *G01N 33/497* (2013.01)

(58) Field of Classification Search
CPC ...... G01N 29/022; G01N 33/497; G01N 5/02; A61B 5/1477; A61B 5/443; C09D 149/00
See application file for complete search history.

(56) References Cited

U.S. PATENT DOCUMENTS 5,501,722 A 3/1996 Toy et al.
9,508,934 B2 11/2016 Kaneko et al.
(Continued)

FOREIGN PATENT DOCUMENTS

CN 103336026 10/2013
CN 103424328 12/2013
(Continued)

OTHER PUBLICATIONS

M.Santonico et al., "Electronic noses calibration procedure in the context of a multicentre medical study", Sensors and Actuators B: Chemical, Aug. 10, 2012, pp. 555-561.
(Continued)

*Primary Examiner* — Francis C Gray
(74) *Attorney, Agent, or Firm* — JCIPRNET

(57) ABSTRACT

An object of the present invention is to provide a resonant sensor having excellent sensitivity and selectivity with respect to a component to be detected that is contained at a low concentration in the system. A resonant sensor of the present invention has a receiving layer that contains a polymer having a repeating unit represented by Formula (1). In Formula (1), $R^1$ represents an alkyl group. A plurality of $R^1$'s may be the same as or different from each other. $R^2$ represents a hydrogen atom, an alkyl group, or an aryl group.

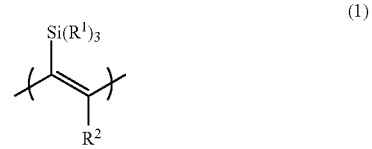

(1)

20 Claims, 2 Drawing Sheets

(51) Int. Cl.
*A61B 5/00* (2006.01)
*C09D 149/00* (2006.01)
*G01N 33/497* (2006.01)

(56) References Cited

U.S. PATENT DOCUMENTS

| | | | |
|---|---|---|---|
| 2007/0059212 A1* | 3/2007 | Masters | G01N 29/036 422/88 |
| 2010/0073016 A1* | 3/2010 | Arora | G01N 33/0057 324/693 |
| 2016/0101386 A1 | 4/2016 | Kumar et al. | |
| 2016/0126460 A1* | 5/2016 | Kaneko | C08G 61/126 526/240 |

FOREIGN PATENT DOCUMENTS

| | | |
|---|---|---|
| CN | 105378962 | 3/2016 |
| EP | 1743691 | 1/2007 |
| JP | S62140606 | 6/1987 |
| JP | H02241529 | 9/1990 |
| JP | 2013068547 | 4/2013 |
| JP | 2013246060 | 12/2013 |

OTHER PUBLICATIONS

"International Search Report (Form PCT/ISA/210) of PCT/JP2018/027636," dated Oct. 30, 2018, with English translation thereof, pp. 1-4.

"Written Opinion of the International Searching Authority (Form PCT/ISA/237) of PCT/JP2018/027636," dated Oct. 30, 2018, with English translation thereof, pp. 1-7.

"Search Report of Europe Counterpart Application", dated Jun. 26, 2020, pp. 1-7.

Office Action of China Counterpart Application, with English translation thereof, dated Dec. 27, 2021, pp. 1-15.

* cited by examiner

RESONANT SENSOR

CROSS-REFERENCE TO RELATED APPLICATIONS

This application is a Continuation of PCT International Application No. PCT/JP2018/027636 filed on Jul. 24, 2018, which claims priority under 35 U.S.C. § 119(a) to Japanese Patent Application No. 2017-146667 filed on Jul. 28, 2017. The above application is hereby expressly incorporated by reference, in its entirety, into the present application.

BACKGROUND OF THE INVENTION

1. Field of the Invention

The present invention relates to a resonant sensor.

2. Description of the Related Art

There is an increasing demand for highly sensitive detection and monitoring of rare gases floating in the air. For example, it is known that exhalation and skin gas contain hydrocarbons and it is considered to use the result of detecting hydrocarbons with a sensor as an index for diagnosing a health condition.

For example, Sensors and Actuators B, 173 (2012), 555-561, discloses that a resonant sensor (specifically, quartz crystal microbalance sensor) having a receiving layer containing a porphyrin-based compound is used to detect hydrocarbons in the system.

SUMMARY OF THE INVENTION

When the present inventors prepared the resonant sensor having a receiving layer containing a porphyrin-based compound disclosed in Sensors and Actuators B, 173 (2012), 555-561, a component to be detected (particularly, hydrocarbon) contained at a low concentration in the system could not be detected with high sensitivity and selectivity.

Accordingly, an object of the present invention is to provide a resonant sensor having excellent sensitivity and selectivity with respect to a component to be detected that is contained at a low concentration in the system.

As a result of intensive investigations on the above object, the present inventors have found that a desired effect can be obtained in a case where a polymer having a predetermined repeating unit is used in a receiving layer, and the present invention has been achieved.

That is, the above object can be achieved by the following configuration.

[1] A resonant sensor comprising:
a receiving layer that contains a polymer having a repeating unit represented by Formula (1) shown below,
in Formula (1), $R^1$ represents an alkyl group, a plurality of $R^1$'s may be the same as or different from each other, and
$R^2$ represents a hydrogen atom, an alkyl group, or an aryl group.

[2] The resonant sensor according to [1] that detects a hydrocarbon.

[3] The resonant sensor according to [2], in which the number of carbon atoms of the hydrocarbon is 1 to 20.

[4] The resonant sensor according to any one of [1] to [3] that detects a component contained in exhalation or skin gas.

[5] The resonant sensor according to any one of [1] to [4], further comprising: another receiving layer, in addition to the receiving layer.

[6] The resonant sensor according to any one of [1] to [5] that detects a change in resonance frequency using a quartz crystal micro-balancing method.

According to the present invention, it is possible to provide a resonant sensor having excellent sensitivity and selectivity with respect to a component to be detected that is contained at a low concentration in the system.

DESCRIPTION OF THE PREFERRED EMBODIMENTS

Figure 1:
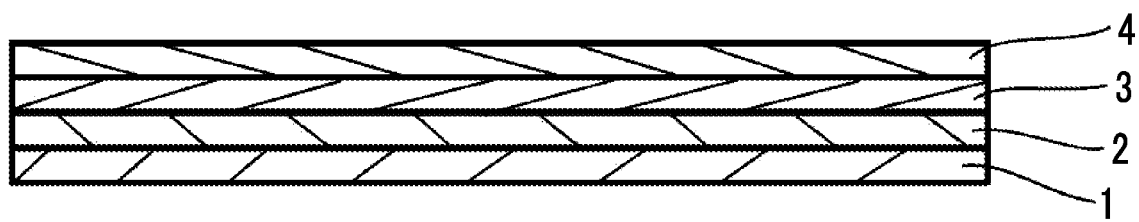
FIG. 1 is a cross-sectional view schematically showing an example of a resonant sensor according to the present invention.

Hereinafter, a resonant sensor according to an embodiment of the present invention will be described.

The constituent requirements described below may be embodied based on the representative embodiments of the present invention. However, the present invention is not limited to such embodiments.

In the present invention, "to" denotes a range including numerical values described before and after "to" as a lower limit value and an upper limit value.

In the present specification, the weight-average molecular weight is defined as a value measured by gel permeation chromatography (GPC) and calculated in terms of polystyrene.

For example, GPC measurement is performed by using HLC-8121GPC (manufactured by Tosoh Corporation), using two items of TSKgel $GMH_{HR}$-H (20) HT (manufactured by Tosoh Corporation, 7.8 mm ID×30 cm) as columns, and using 1,2,4-trichlorobenzene as an eluent. In addition, GPC measurement is performed by using an infrared (IR) detector under the conditions in which the sample concentration is 0.02% by mass, the flow rate is 1.0 ml/min, the sample injection amount is 300 µl, and the measurement temperature is 160° C.

In the present specification, the unit "ppm" means "parts-per-million ($10^{-6}$)" and the unit "ppt" means "parts-per-trillion ($10^{-12}$)".

A resonant sensor according to an embodiment of the present invention has a receiving layer containing a polymer having a repeating unit represented by Formula (1) shown below (hereinafter, also referred to as "specific polymer").

The resonant sensor according to the embodiment of the present invention detects a component to be detected as a result of adsorption of the component to be detected onto the receiving layer through a certain interaction between the specific polymer contained in the receiving layer and the component to be detected.

The resonant sensor according to the embodiment of the present invention has excellent sensitivity and selectivity with respect to a component to be detected (particularly, hydrocarbon) that is contained at a low concentration in the system. Although the reason for this has not been clarified, the detection capability of the resonance sensor for a trace component and the adsorption capability of the specific polymer for a component to be detected contained in the receiving layer act synergistically to exhibit high sensitivity that has not been achieved so far, and the potential of molecular recognition ability of specific polymer is exhibited.

[Specific Polymer]

The specific polymer is a polymer having a repeating unit represented by Formula (1).

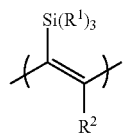

$R^1$ represents an alkyl group.

The alkyl group may be linear or branched or may have a cyclic structure, and from the viewpoint of increasing the sensitivity and selectivity with respect to the component to be detected (particularly, hydrocarbon) contained at a low concentration in the system, the alkyl group is preferably linear or branched and more preferably linear.

The number of carbon atoms of the alkyl group is preferably 1 to 8, more preferably 1 to 6, and particularly preferably 1 to 4 from the viewpoint of further increasing the sensitivity and selectivity with respect to the component to be detected (particularly, hydrocarbon) at a low concentration.

A plurality of $R^1$'s may be the same as or different from each other.

$R^2$ represents a hydrogen atom, an alkyl group, or an aryl group, and from the viewpoint of further increasing the sensitivity and selectivity with respect to the component to be detected (particularly, hydrocarbon) at a low concentration, a hydrogen atom or an alkyl group is preferable and an alkyl group is particularly preferable.

The definition and preferable aspect of the alkyl group in $R^2$ are the same as those in $R^1$. However, the alkyl group in $R^2$ may have a substituent such as a silyl group. In a case where the alkyl group in $R^2$ has a substituent, the number of carbon atoms of the substituent is not included in the number of carbon atoms of the alkyl group.

The aryl group may be monocyclic or polycyclic, but from the viewpoint of further increasing the sensitivity and selectivity with respect to the component to be detected (particularly, hydrocarbon) at a low concentration, the aryl group is preferably monocyclic.

The aryl group may be unsubstituted or may have a substituent. In a case where the aryl group has a substituent, specific examples of the substituent include a halogen atom (for example, a chlorine atom, a fluorine atom, or a bromine atom), an alkyl group, and a halogenated alkyl group.

From the viewpoint of further increasing the sensitivity and selectivity with respect to the component to be detected (particularly, hydrocarbon) at a low concentration, the number of carbon atoms of the aryl group is preferably 6 to 20, more preferably 6 to 14, and particularly preferably 6 to 8. In the present specification, in a case where the aryl group has a substituent, the number of carbon atoms of the substituent is not included in the number of carbon atoms of the aryl group.

Specific examples of the aryl group include a phenyl group, a benzyl group, a phenethyl group, a tolyl group, a naphthyl group, and a biphenyl group.

The content of the repeating unit represented by Formula (1) with respect to all the repeating units of the specific polymer is preferably 20 to 100 mol % and particularly preferably 50 to 100 mol % from the viewpoint of further improving the sensitivity and selectivity of the resonant sensor.

The weight-average molecular weight of the specific polymer is preferably 10,000 to 5,000,000 and particularly preferably 50,000 to 2,000,000 from the viewpoint of further improving the sensitivity and selectivity of the resonant sensor.

The specific polymer may contain a repeating unit other than the repeating unit represented by Formula (1).

Specific examples of the specific polymer are shown below.

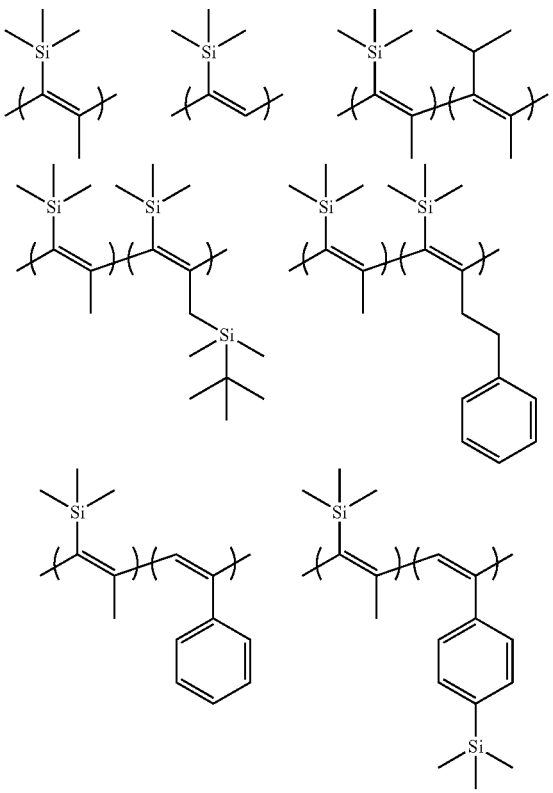

[Embodiment of Sensor]
<Receiving Layer>

The resonant sensor according to the embodiment of the present invention has a receiving layer containing a specific polymer. As long as the resonant sensor according to the embodiment of the present invention has a predetermined receiving layer, the configuration thereof is not particularly limited. However, the resonant sensor preferably has at least a resonant sensor main body and a receiving layer containing a specific polymer. The resonant sensor may have members other than the predetermined receiving layer and the resonant sensor main body.

The content of the specific polymer in the receiving layer varies depending on the embodiment of the resonant sensor, but the content is preferably 10% to 100% by mass, more preferably 30% to 100% by mass, and particularly preferably 50% to 100% by mass with respect to the total mass of the receiving layer.

A method of forming the receiving layer containing a specific polymer is not particularly limited and examples thereof include a method of applying a composition obtained by dissolving a specific polymer in a solvent (such as tetrahydrofuran) to the surface on which the receiving layer containing a specific polymer is formed and further drying the obtained coating film to form a film.

The film thickness of the receiving layer containing a specific polymer varies depending on the embodiment of the resonant sensor and is preferably 10 nm to 100 µm, more preferably 50 nm to 50 µm, and particularly preferably 100 nm to 10 µm.

It is preferable that the resonant sensor according to the embodiment of the present invention further has another receiving layer in addition to the receiving layer containing a specific polymer. In a case where the resonant sensor has another receiving layer having different properties, for example, there are advantages such as that other components can be detected and the measurement accuracy for a composite gas can be improved. The receiving layer containing a specific polymer and another receiving layer may be separately arranged or may be laminated.

Specific examples of another receiving layer include receiving layers formed of hydrophilic compounds (for example, polyvinyl pyrrolidone). Thus, since the resonant sensor has a hydrophobic receiving layer containing a specific polymer and a hydrophilic receiving layer, it is possible to detect various components.

<Resonant Sensor>

The resonant sensor according to the embodiment of the present invention adsorbs a specific type of gas molecule contained in the air onto the surface, and takes the presence or absence of adsorption or the amount of adsorption as the amount of change (specifically, decrease amount) in the resonance frequency of the dielectric material (piezoelectric material) to be resonantly driven so as to detect the target gas. That is, the resonant sensor is a sensor using a mass micro-balancing method.

FIG. 1 is a cross-sectional view schematically showing an example of a laminate structure in the resonant sensor according to the embodiment of the present invention. The resonant sensor shown in FIG. 1 has a laminate structure in which a first electrode 1, a dielectric material 2, a second electrode 3, and a receiving layer 4 containing a specific polymer are provided in this order. In addition, a substrate for supporting the resonant sensor may be provided on a surface of the first electrode 1 opposite to the dielectric material 2. In a case where the dielectric material is of a self-oscillation type, the substrate is not required. On the other hand, in a case where the dielectric material is a ceramic piezoelectric element or the like, the substrate is required to resonantly drive the element.

Figure 2:
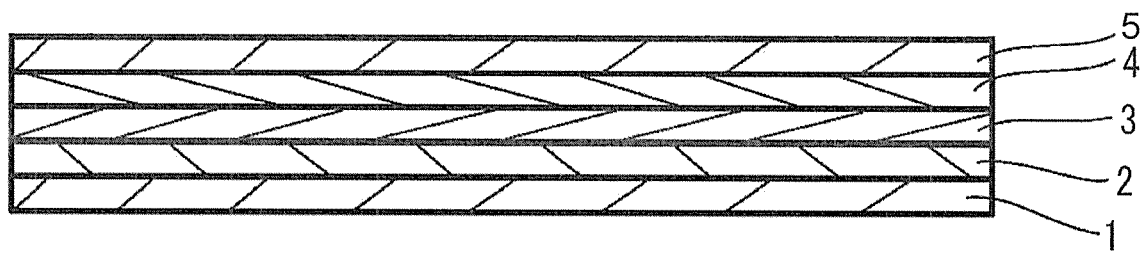
FIG. 2 is a cross-sectional view schematically showing another example of a resonant sensor according to the present invention.

FIG. 2 is a cross-sectional view schematically showing another example of a laminate structure in the resonant sensor according to the embodiment of the present invention. The resonant sensor shown in FIG. 2 has the same structure as the resonant sensor shown in FIG. 1. The difference is that the resonant sensor shown in FIG. 2 has another receiving layer 5 above the receiving layer 4.

In the sensing by the mass micro-balancing method, a voltage is applied to a fine dielectric material (piezoelectric material) to vibrate the dielectric material at a constant frequency (resonance frequency), and the mass increase due to gas adsorption onto the surface of the dielectric material is detected as a change (specifically, decrease) in the resonance frequency. As a representative example of a resonant sensor using a mass micro-balancing method, there is known a sensor using a quartz crystal mass micro-balancing (QCM) method using a crystal as a dielectric material for resonance driving (hereinafter also referred to as a "QCM sensor").

The QCM sensor is usually provided with electrodes on both sides of a crystal thin film cut at a specific angle (AT-cut), and a voltage is applied to cause shear vibration at a resonance frequency in the horizontal direction with the crystal surface. Since this resonance frequency decreases with the mass of gas adsorbed on the electrode, a change in mass of the substance on the electrode can be captured. The QCM sensor itself having a crystal vibrator including crystals and an electrode sandwiched between the crystals is known, and can be produced by a normal method or a commercially available product may be used.

A QCM sensor as one embodiment of the resonant sensor of the present invention preferably has a receiving layer containing a specific polymer for adsorbing a component to be detected onto the surface of one electrode of a pair of electrodes provided to sandwich a dielectric material therebetween. That is, as the resonant sensor according to the embodiment of the present invention, a QCM sensor having a crystal resonator and a receiving layer arranged on the crystal resonator is preferable. The mass of the component to be detected, which is adsorbed onto the receiving layer containing a specific polymer, is detected as a change (specifically, decrease) in the resonance frequency of the crystal vibrator to be resonantly driven.

The electrode used in the resonant sensor is not particularly limited and a metal material or the like usually used as an electrode can be used.

In addition to the QCM sensor as the resonant sensor, a resonant sensor formed of a ceramic dielectric (piezoelectric material) without using a crystal or quartz as the dielectric material can be employed. Examples of such sensors include a cantilever type sensor and a surface acoustic wave (SAW) sensor. Since a ceramic dielectric material can be formed on a substrate by using a sputtering method, a vacuum deposition method, or the like, there is an advantage that the ceramic dielectric material can be applied to prepare a sensor using a micro electro mechanical system (MEMS) technology. Examples of such ceramic dielectric materials include lead zirconate titanate (PZT), lead zirconate titanate doped with niobium (PZTN), zinc oxide (ZnO), and aluminum nitride (AlN).

In a cantilever type sensor, electrodes are arranged on both sides of a film formed of the above-mentioned ceramic dielectric material, and a specific voltage is applied between the electrodes to resonantly drive the ceramic dielectric material. In a case where a resonant sensor formed of a ceramic dielectric material is used as the resonant sensor according to the embodiment of the present invention, it is preferable to arrange a receiving layer containing a specific polymer for adsorbing a component to be detected on the surface of one electrode of the pair of electrodes provided to sandwich the dielectric material therebetween. The mass of the component to be detected, which is adsorbed onto the receiving layer containing a specific polymer, is detected as a change (specifically, decrease) in the resonance frequency of the ceramic dielectric material to be resonantly driven.

[Use]

The use of the resonant sensor according to the embodiment of the present invention is not particularly limited and for example, the resonant sensor may be used for exhalation or skin gas inspection, odor quantitative measurement, gas leak inspection, and environmental investigation.

Here, the resonant sensor according to the embodiment of the present invention can detect a component to be detected (particularly, hydrocarbon) that is contained at a low concentration in the system with high sensitivity and high selectivity. Therefore, the resonant sensor according to the embodiment of the present invention is particularly suitable for inspection for exhalation gas or skin gas in which a component to be detected is contained at a low concentration. Here, the skin gas in the present invention is a general term for volatile substances that are emitted from the body surface.

In addition, as a specific example of a case where the component to be detected is contained at a low concentration in the system, a case where a gas as the component to be detected exists in the system in a range of 1 vol ppt to 100 vol ppm may be exemplified. It is more preferable that the resonant sensor according to the embodiment of the present invention detects the component to be detected contained at a lower concentration in the system in a range of 1 vol ppt to 10 vol ppm with high sensitivity and selectivity, and it is particularly preferable that the resonant sensor according to the embodiment of the present invention detects the component to be detected contained at a more lower concentration in the system in a range of 1 vol ppt to 1 vol ppm with high sensitivity and selectivity.

[Component to Be Detected]

In a case where the component to be detected is contained at a low concentration in the system, the component to be detected of the resonant sensor according to the embodiment of the present invention is preferably a hydrocarbon from the viewpoint of being capable of detecting the component with higher sensitivity and higher selectivity.

In the present specification, the hydrocarbon means a compound formed of only carbon and hydrogen.

The number of carbon atoms of the hydrocarbon is preferably 1 to 20, more preferably 2 to 15, and particularly preferably 4 to 10. Thus, the hydrocarbon contained at a low concentration in the system can be detected with high sensitivity and high selectivity.

The hydrocarbon may be linear or branched, or may have a cyclic structure. Specific examples of the hydrocarbon include saturated aliphatic hydrocarbons, unsaturated aliphatic hydrocarbons, and aromatic hydrocarbons.

Specific examples of saturated aliphatic hydrocarbons include n-heptane, dimethylpentane, and cyclopentane. Specific examples of unsaturated aliphatic hydrocarbons include isoprene. Specific examples of aromatic hydrocarbons include toluene.

EXAMPLES

Hereinafter, the present invention will be described in detail using Examples. However, the present invention is not limited thereto. Unless otherwise specified, the formulation amount of each component is based on mass.

Example 1

A solution obtained by dissolving 15 mg of poly(1-trimethylsilyl-1-propyne) (manufactured by Gelest Inc.) in 40 g of tetrahydrofuran (THF, manufactured by Wako Pure Chemical Industries, Ltd.) was prepared. The obtained solution was added dropwise to one surface of a crystal vibrator in a QCM sensor (quartz crystal microbalance, manufactured by Tamadevice. Co. Ltd.) and further dried at room temperature to form a film formed of poly(1-trimethylsilyl-1-propyne) as a receiving layer.

The QCM sensor having the receiving layer obtained was put into a flow cell, various test gases shown below were allowed to pass using nitrogen gas as a carrier, and the sensitivity and selectivity of the QCM sensor having the receiving layer with respect to the component to be detected were evaluated. The results are shown in Table 1.

Comparative Example 1

A QCM sensor having a receiving layer formed of a tetrakis(butoxyphenyl)porphyrin copper complex was obtained in the same manner as in Example 1 except that poly(1-trimethylsilyl-1-propyne) was changed to a tetrakis(butoxyphenyl)porphyrin copper complex described in Sensors and Actuators B, 173 (2012), 555-561.

The sensitivity and selectivity of the QCM sensor having the receiving layer with respect to the component to be detected were evaluated in the same manner as in Example 1. The results are shown in Table 1.

Comparative Example 2

A QCM sensor having a receiving layer formed of polyisobutylene was obtained in the same manner as in Example 1 except that poly(1-trimethylsilyl-1-propyne) was changed to polyisobutylene.

The sensitivity and selectivity of the QCM sensor having the receiving layer with respect to the component to be detected were evaluated in the same manner as in Example 1. The results are shown in Table 1.

[Evaluation]

<Sensitivity>

Based on the absolute value of the frequency change occurred in the QCM sensor having the receiving layer in a case where a predetermined amount of test gas containing 1 vol ppm of n-heptane was allowed to flow, the sensitivity was evaluated according to the standards shown below. Here, as the absolute value of the frequency change increases, the sensitivity of the QCM sensor becomes further excellent.

5: 100 Hz or more

4: 70 Hz or more and less than 100 Hz

3: 40 Hz or more and less than 70 Hz

2: 10 Hz or more and less than 40 Hz

1: Less than 10 Hz

<Selectivity>

A ratio (RN/RA) of the absolute value (RA [Hz]) of the frequency change of the QCM sensor in a case where a predetermined amount of test gas containing 1 vol ppm of n-heptane was allowed to flow with respect to the absolute value (RN [Hz]) of the frequency change of the QCM sensor in a case where a predetermined amount of test gas containing 1 vol ppm of acetone was allowed to flow was calculated and the selectivity of the QCM sensor with respect to hydrocarbon (n-heptane) was evaluated according to the standards shown below. As the value of the ratio increases, the selectivity of the QCM sensor becomes further excellent.

5: 20 or more

4: 13 or more and less than 20

3: 6 or more and less than 13

2: 2 or more and less than 6

1: Less than 2

The results of the above evaluation tests are shown in Table 1.

TABLE 1

| | Constitutional component of receiving layer | Evaluation result | |
|---|---|---|---|
| | | Sensitivity (component to be detected: n-heptane) | Selectivity (RN/RA) |
| Example 1 | Poly(1-trimethylsilyl-1-propyne) | 5 | 5 |
| Comparative Example 1 | Tetrakis(butoxy-phenyl)porphyrin copper complex | 2 | 1 |
| Comparative Example 2 | Polyisobutylene | 1 | 2 |

As shown in Table 1, in the comparison of the QCM sensor (Example 1) having the receiving layer containing the polymer having the repeating unit represented by Formula (1) and the QCM sensors (Comparative Examples 1 and 2) having the receiving layer containing a polymer having other than the above polymer, it was found that the hydrocarbon contained at a low concentration in the system can be detected with high sensitivity and high selectivity.

EXPLANATION OF REFERENCES

1: first electrode
2: dielectric material (piezoelectric material)
3: second electrode
4: receiving layer containing specific polymer

What is claimed is:

1. A resonant sensor for detecting a component contained at a low concentration, the resonant sensor comprising:
    a receiving layer that contains a polymer having a repeating unit represented by Formula (1),

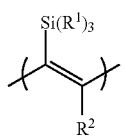

(1)

in Formula (1), $R^1$ represents an alkyl group, a plurality of $R^1$'s may be the same as or different from each other, and
$R^2$ represents a hydrogen atom, an alkyl group, or an aryl group.

2. The resonant sensor according to claim 1, wherein the component to be detected by the resonant sensor comprises a hydrocarbon.

3. The resonant sensor according to claim 2,
    wherein a number of carbon atoms of the hydrocarbon in the component to be detected by the resonant sensor is configured to be 1 to 20.

4. The resonant sensor according to claim 1, wherein the component to be detected by the resonant sensor is configured to be contained in exhalation gas or skin gas.

5. The resonant sensor according to claim 1, further comprising:
    another receiving layer, in addition to the receiving layer, being configured to have different properties than a property of the receiving layer and being configured to detect different components than the component being detected using the receiving layer.

6. The resonant sensor according to claim 1 that detects a change in resonance frequency of the resonant sensor to detect a change in mass of the component being detected using a quartz crystal micro-balancing method.

7. The resonant sensor according to claim 2, wherein the component to be detected by the resonant sensor is configured to be contained in exhalation gas or skin gas.

8. The resonant sensor according to claim 3, wherein the component to be detected by the resonant sensor is configured to be contained in exhalation gas or skin gas.

9. The resonant sensor according to claim 2, further comprising:
    another receiving layer, in addition to the receiving layer, being configured to have different properties than a property of the receiving layer and being configured to detect different components than the component being detected using the receiving layer.

10. The resonant sensor according to claim 3, further comprising:
    another receiving layer, in addition to the receiving layer, being configured to have different properties than a property of the receiving layer and being configured to detect different components than the component being detected using the receiving layer.

11. The resonant sensor according to claim 4, further comprising:
    another receiving layer, in addition to the receiving layer, being configured to have different properties than a property of the receiving layer and being configured to detect different components than the component being detected using the receiving layer.

12. The resonant sensor according to claim 7, further comprising:
    another receiving layer, in addition to the receiving layer, being configured to have different properties than a property of the receiving layer and being configured to detect different components than the component being detected using the receiving layer.

13. The resonant sensor according to claim 8, further comprising:
    another receiving layer, in addition to the receiving layer, being configured to have different properties than a property of the receiving layer and being configured to detect different components than the component being detected using the receiving layer.

14. The resonant sensor according to claim 2 that detects a change in resonance frequency of the resonant sensor to detect a change in mass of the component being detected using a quartz crystal micro-balancing method.

15. The resonant sensor according to claim 3 that detects a change in resonance frequency of the resonant sensor to detect a change in mass of the component being detected using a quartz crystal micro-balancing method.

16. The resonant sensor according to claim 4 that detects a change in resonance frequency of the resonant sensor to detect a change in mass of the component being detected using a quartz crystal micro-balancing method.

17. The resonant sensor according to claim 5 that detects a change in resonance frequency of the resonant sensor to detect a change in mass of the component being detected using a quartz crystal micro-balancing method.

18. The resonant sensor according to claim 7 that detects a change in resonance frequency of the resonant sensor to detect a change in mass of the component being detected using a quartz crystal micro-balancing method.

19. The resonant sensor according to claim 8 that detects a change in resonance frequency of the resonant sensor to detect a change in mass of the component being detected using a quartz crystal micro-balancing method.

20. The resonant sensor according to claim 9 that detects a change in resonance frequency of the resonant sensor to detect a change in mass of the component being detected using a quartz crystal micro-balancing method.

\* \* \* \* \*